United States Patent [19]
> Ujimoto et al.

[11] Patent Number: 5,064,489
[45] Date of Patent: Nov. 12, 1991

[54] METHOD FOR MAKING DISPOSABLE ABSORBENT GARMENTS

[75] Inventors: Hiroshi Ujimoto, Kawanoe; Hironori Nomura, Iyomishima; Toshinori Yamamoto, Kawanoe, all of Japan

[73] Assignee: Uni-Charm Corporation, Ehime, Japan

[21] Appl. No.: 475,163

[22] Filed: Feb. 5, 1990

Related U.S. Application Data

[63] Continuation of Ser. No. 286,170, Dec. 19, 1988, abandoned.

[30] Foreign Application Priority Data

Dec. 19, 1987 [JP] Japan ................. 62-321935

[51] Int. Cl.$^5$ ..................... A61F 13/16; B29C 65/72
[52] U.S. Cl. ....................... 156/164; 604/385.2
[58] Field of Search ............. 156/164, 182, 201, 202, 156/324; 604/385.1, 385.2

[56] References Cited

U.S. PATENT DOCUMENTS

| 4,081,301 | 3/1978 | Buell | 156/164 |
| 4,648,928 | 3/1987 | Alex | 156/164 |
| 4,655,760 | 4/1987 | Morman et al. | 604/385.2 |
| 4,695,278 | 9/1987 | Lawson | 604/385.2 |
| 4,753,643 | 6/1988 | Kassai | 604/385.1 |
| 4,822,435 | 4/1989 | Igaue et al. | 156/164 |
| 4,834,740 | 5/1989 | Suzuki et al. | 604/385.2 |

FOREIGN PATENT DOCUMENTS 0219326 4/1987 European Pat. Off. .
0243013 10/1987 European Pat. Off. .
1326564 12/1963 France .

Primary Examiner—Michael W. Ball
Assistant Examiner—Steven D. Maki
Attorney, Agent, or Firm—Fred Philpitt

[57] ABSTRACT

In a method for making disposable absorbent garments, elastic flaps which are brought in close contact around the wearer's legs are formed separately from a topsheet and a backsheet and bonded to the topsheet which is being transferred to an assembly line before the topsheet is placed upon the backsheet.

4 Claims, 3 Drawing Sheets

METHOD FOR MAKING DISPOSABLE ABSORBENT GARMENTS

This is a continuation of application Ser. No. 286,170, now abandoned, filed Dec. 19, 1988 and the benefits of 35 USC 120 are claimed relative to it.

BACKGROUND OF THE INVENTION

The present invention relates to a method for making absorbent garments such as diaper and, more particularly, to a method for attaching elastic flaps to such garments along opposite sides so as to be brought in close contact around the wearer's legs when put on.

In making of disposable diaper, elastic flaps have usually been formed on the opposite sides of an individual diaper by construction each elastic flap into a unique configuration or by selecting the material for the elastic flaps differing from those for a liquid-permeable topsheet and/or a liquid-impermeable backsheet of the diaper to achieve a high air-permeability of the elastic flaps. Thus, it is known to provide the diaper on the opposite sides thereof with the elastic flaps made of a sheet formed separately from the topsheet and/or the backsheet. In such a diaper, the absorbent cores have usually been interposed between the topsheet and the backsheet to form a main body of diaper and then the side flaps have been bonded to the topsheet and/or the backsheet on the opposite sides thereof.

However, the procedure in which, upon formation of the main body of diaper, the elastic flaps are bonded thereto sometimes prevents said bonding of the elastic flaps from being reliably and orderly achieved, because the main body of the diaper comprises a layered structure. As a result, not only the appearance is deteriorated but also the region of diaper occupied by the elastic flaps is subject to a tensile force higher than that exerted on the remaining region and, in an extreme case, the areas along which the elastic flaps are bonded to the main body of diaper may be torn, causing excretion leakage.

It is conceivable that, in order to assure said bonding, relatively large amount of adhesive is applied between the elastic flaps and the topsheet and/or the backsheet, or these components are welded together or adhesive is used with welding.

However, when the elastic flaps are bonded to at least a part of the topsheet, application of said relatively large amount of adhesive might disadvantageously result in that excessive adhesive exudes onto the outer surface, adversely affecting the wearer's skin. Furthermore, use of said welding might do damage to a part (i.e., said bonded areas) of the backsheet, since the backsheet is usually made of extremely thin plastic film having a relatively low melting point, such as polyethylene film.

SUMMARY OF THE INVENTION

The object of this invention is, in view of the problems as have been mentioned just above, to provide an improved method for making disposable absorbent garments comprising steps of forming a cover unit by bonding the elastic flaps to the topsheet and then bonding this cover unit to the backsheet.

This object is achieved, in accordance with the present invention, by a method for making disposable absorbent garments, the method comprising steps of: transferring a liquid-permeable continuous topsheet having transversely opposite side edges to an assembly line; feeding each continuous elastic flap, maintained in a stretched condition, longitudinally thereof to a location adjacent corresponding one of transversely opposite sides of the continuous topsheet; bonding the each elastic flap to the continuous topsheet along at least one longitudinal lien adjacent corresponding one of the transversely opposite sides thereof, thereby forming at least one portion of the flap adapted to rise on the bonded line under elastic contractive force of the elastic flap; intermittently disposing absorbent cores on a liquid-impermeable continuous backsheet being transferred to the assembly line along a central zone thereof or on a side of the cover unit comprising the continuous topsheet and the continuous elastic flaps, the side being opposed to the side on which the continuous flaps are bonded to the continuous topsheet, along a central zone of said cover unit; forming a continuous garment unit by placing the one of the cover unit and the backsheet on which the core are not disposed upon the other of the cover unit and the backsheet on which the cores are disposed and then at least bonding the cover unit to the backsheet, and transversely cutting the garment unit along lines each defined between each pair of adjacent cores.

Preferably, the elastic flap is provided with a desired elasticity by attaching an elastic band to the flap along a location thereof corresponding to a free end of the flap portion before the elastic flap is bonded to the topsheet.

Preferably, bonding of the elastic flaps to the topsheet is achieved by an adhesive applied line and a welded line both extending longitudinally of these components so that the welded line extend inside the adhesive applied line in each completed diaper. The welded line is formed by a heat treatment or a supersonic wave treatment.

Bonding of the elastic flap to the topsheet is performed so that the outer side portion of the flap extends or not beyond the outer side edge of the topsheet. In the case of the outer side portion extending beyond the outer side edge of the topsheet, this extension terminates at the outer side edge of the backsheet and the extension is bonded to the outer side portion of the backsheet so that the elastic band extends along the innermost side of the elastic flap.

According to the method for the present invention, the elastic flaps are formed separately from the topsheet and the backsheet but bonded to the topsheet which is independently being transferred to the assembly line before the topsheet is placed upon the backsheet. Accordingly, bonding of the elastic flaps can be achieved more reliably, more orderly and a higher speed than when the elastic flaps are bonded to the main body of diaper in the course of transferring the topsheet and the backsheet together with the cores interposed therebetween to the assembly line.

The elastic flaps are bonded to the topsheet before the topsheet is bonded to the backsheet generally made of material unsuitable for welding, as mentioned above, in the method of the invention, so it is possible to utilize both adhesive and welding. Thus, the bonding strength of the elastic flaps can be improved by adopting both adhesive and welding. Furthermore, bonding may be performed so that the welded line extends inside the adhesive applied line in the complete diameter so as to prevent adhesive from exuding onto the outer surface of the topsheet portion extending inside the welded line and thereby adversely affecting the wearer's skin.

PREFERRED EMBODIMENTS

Figure 1:
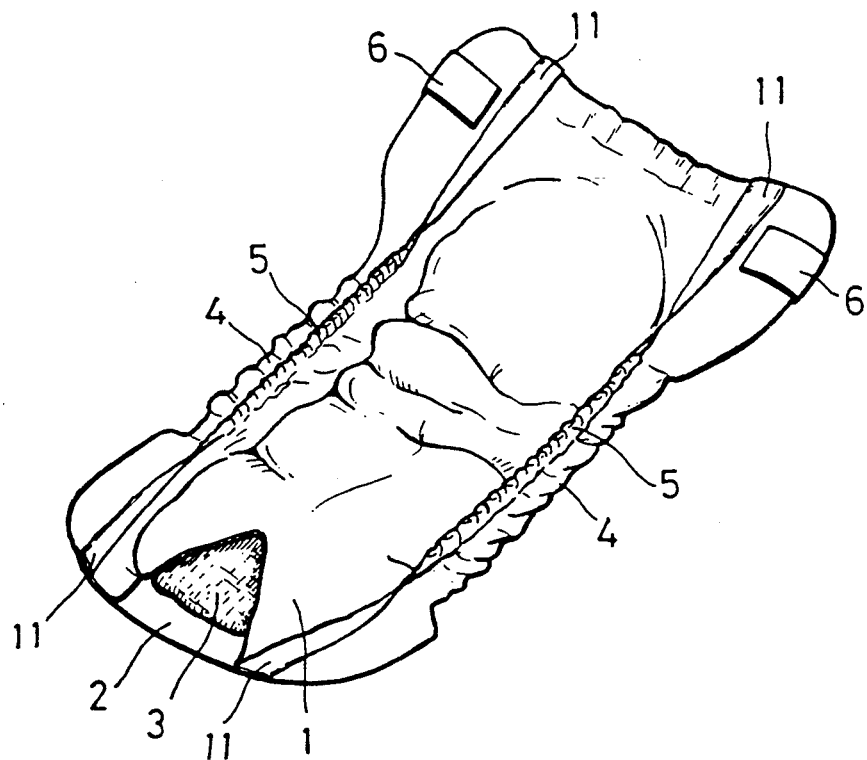
FIG. 1 is a partially broken away perspective view of the diaper completed by a first embodiment of the method according to the present invention.
Figure 2:
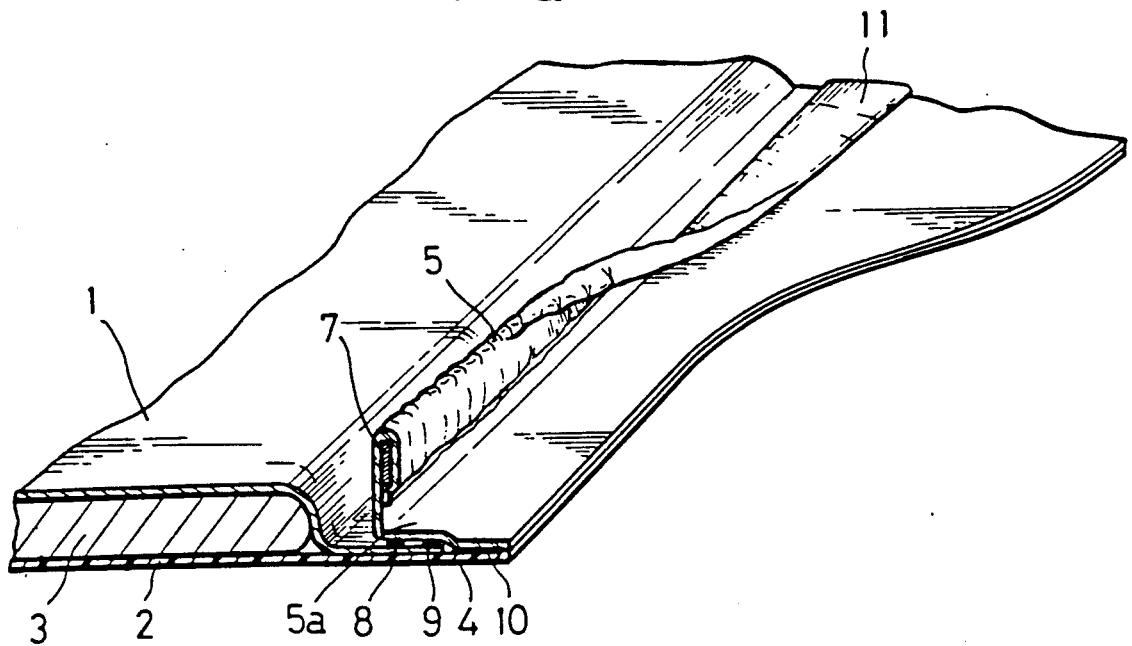
FIG. 2 is a perspective view showing, partially in section, the side flap zone of said diaper.

FIGS. 1 and 2 show a disposable diaper as an example of garments formed by the method according to the present invention.

This diaper includes a liquid-permeable topsheet 1, a liquid-impermeable backsheet 2, a liquid-absorbent core 3 interposed between the sheets 1, 2, flaps 4 extending outwards from laterally opposite sides of the core 3, elastic flaps 5 attached to the respective flaps 4, and tape fasteners 6 attached to outer edges of the respective elastic flaps 5 at locations adjacent respective longitudinal one ends of the outer edges so that the locations on the respective elastic flaps 5 are opposed to each other. Each flap 5 has been made elastic by attaching an elastic band 7 to a substantially non-elastic narrow sheet along one side laterally of this sheet. A transversely intermediate zone of each flap 5 is bonded to the corresponding one of transversely opposed sides of the topsheet 1 by an inner welded line 8 and an outer adhesive applied line 9 while a transversely outer side of each flap 5 is bonded to the corresponding one of transversely opposed sides of the backsheet 2 by an adhesive applied line 10, and longitudinally opposed ends 11 of each flap 5 are bonded, by adhesive or welding, to surfaces against which the respective ends 11 bear at this flap 5 is outwardly brought down. In this way, a longitudinally intermediate portion of each flap 5 rises on a welded base 5a along which the flap 5 is bonded to the corresponding flap 4 so far as the elastic band is in a contracted condition, and thereby will be brought in close contact around the wearer's legs, when put on, for effective prevention of excretion leakage.

Figure 3:
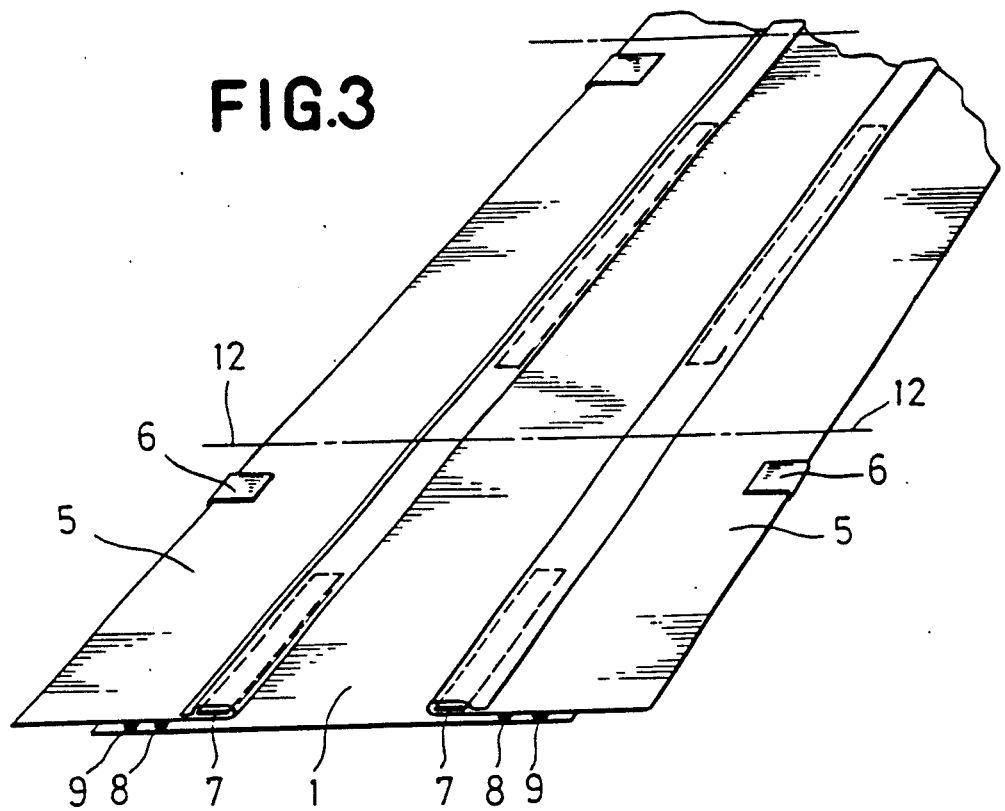
FIGS. 3 and 4 are perspective views schematically illustrating steps of forming the diaper.
Figure 4:
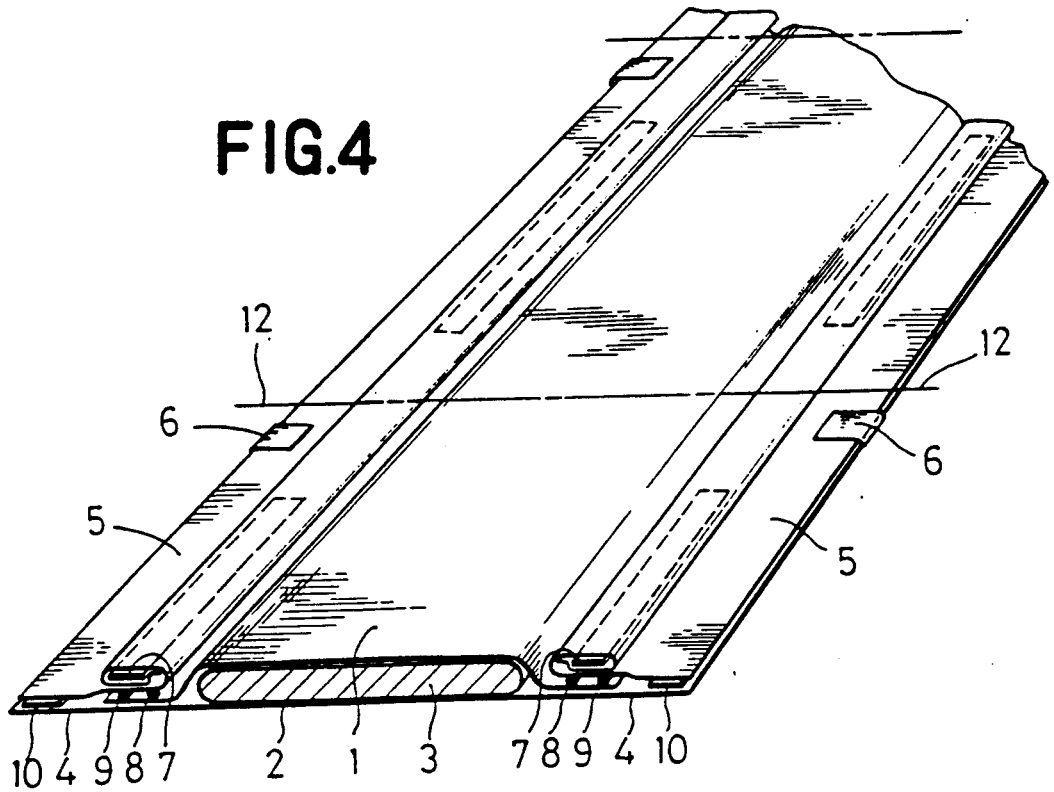

FIGS. 3 and 4 schematically illustrate steps taken to execute the method according to the present invention.

The elastic band 7 maintained stretched is intermittently bonded by adhesive (not shown) to each continuous elastic flap 5 along its transversely one side so that the elastic band 7 is disposed longitudinally of the elastic flap 5, and this elastic band 7 is enclosed by the side edges of said flap 5, on one hand, and the tape fasteners 6 are attached at longitudinally regular intervals to the transversely other side of said flap 6, on the other hand. A pair of the flaps 5 thus formed, which are spaced by a predetermined distance from each other and have their portions containing the elastic bands 7 disposed on inner sides of the respective flaps 5, are transferred to the assembly line (not shown) of diaper components. In the course of transfer, the transversely intermediate zones of the respective flaps 5 are bonded to the transversely opposed sides of the continuous topsheet 1 being transferred to the assembly line by the respective inner welded lines 8 and the respective adhesive applied lines 9.

A continuous cover unit thus formed by the topsheet 1 and the flaps 5 bonded thereto is placed on another continuous member, also being transferred to the assembly line, comprising the backsheet 2 on which the absorptive cores 3 have been disposed at regular intervals longitudinally of the backsheet 2 so that the cores 3 are interposed between the topsheet 1 and the backsheet 2 on the assembly line. Then, the transversely one side of each flap 5 is bonded to the corresponding one of transversely opposed sides of the backsheet 2 by an adhesive 10 previously applied to one of these components 2, 5. Thus, a continuous diaper unit comprising a series of individual diapers are formed and, to form the individual diapers into a predetermined configuration, opposite sides of each individual diaper are partially cut away (see FIG. 1) and the diaper unit is transversely cut along liens 12 each defined between each pair of adjacent cores 3. In this manner, the individual complete diapers are obtained. To sandwich the cores 3 between the topsheet 1 and the backsheet 2, the cores 3 may be serially disposed on one of these sheets, preferably on the backsheet 2, and the topsheet 1 may be placed on this subassembly.

Figure 5:
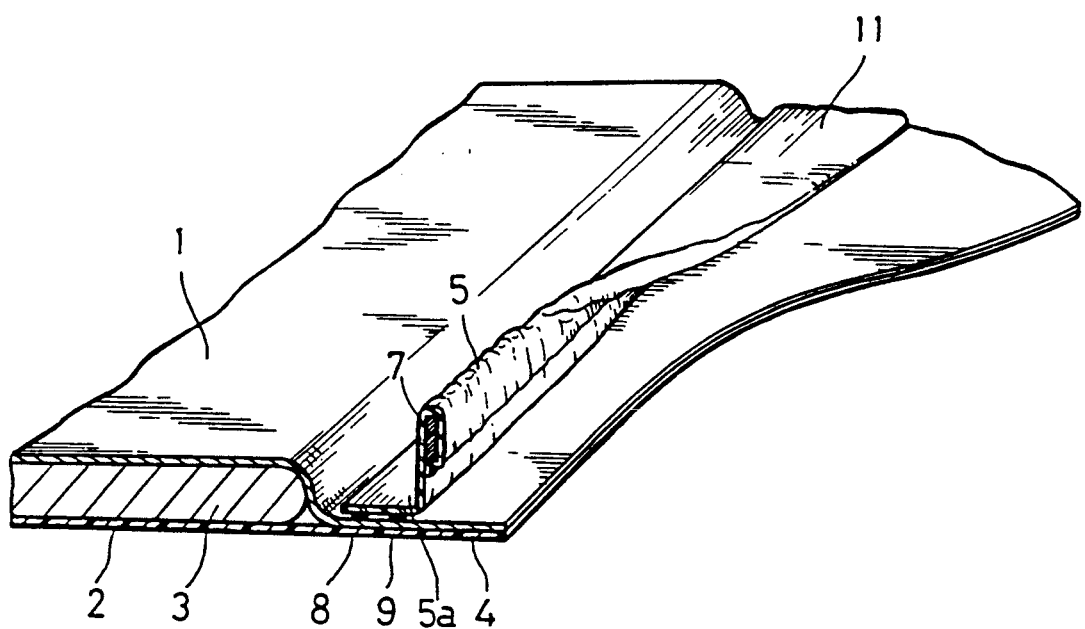
FIG. 5 is a view similar to FIG. 2 but showing the side flap zone of the diaper formed by another embodiment of the method according to the present invention.

FIG. 5 shows another embodiment of the method according to the present invention.

In this embodiment, the bonded base 5a of each elastic flap 5 extends inside a portion of said flap 5 which rises, but such arrangement causes no substantial difference of the effect obtained by the present invention in comparison with the previously mentioned embodiment and is well covered by the present invention.

The tape fasteners 6 may be attached to the flaps 4 and/or the flaps 5 during the forming process or at the other suitable time point.

Material for the flap 5 includes air-permeable plastic film, laminate of the film and nonwoven fabric, and water-proof treated nonwoven fabric and porous plastic film; material for the backsheet 2 includes air-permeable plastic film and laminate of the film and nonwoven fabric; material for the core 3 includes fluffy pulp; and mixture of the fluffy pulp and highly absorptive polymer; and material for the elastic band 7 includes polyurethane foam, rubber, and plastic film adapted to be contracted by a heat treatment.

What is claimed is:

1. A method for making disposable absorbent articles, the method comprising the steps of:
    (a) transferring a liquid-permeable continuous topsheet (1) to an assembly point, said topsheet having a topside, a bottom side and spaced apart side edges,
    (b) feeding two continuous elastic flaps (5) that each contain an elastic band (7), to spaced apart locations adjacent each of said side edges of said continuous topsheet (1), each elastic band being maintained in a stretched condition;
    (c) forming a cover unit having a top side and a bottom side by first heat welding each elastic flap (5) to the continuous topsheet (1) along longitudinal liens (8) adjacent the side edges of said continuous topsheet (1), and thereafter further bonding spaced apart end portions of each flap (5) into oppositely directed essentially flat positions so that the portion of each flap (5) that is between said spaced apart end portions can rise to an essentially vertical position because of the tendency of each elastic band to contract, thereby allowing an intermediate portion of each flap (5) to rise on the bonding line under the elastic contractive force of the elastic band (7);

(d) intermittently disposing absorbent cores (3) on the topside of a liquid-impermeable continuous backsheet (2) having a topside, bottom side and two side edges, and which is wider than said topsheet (1), to thereby form a continuous backsheet unit having a topside and a bottom side, and then transferring this continuous backsheet unit to an assembly line, (e) forming on the assembly line a continuous absorbent article by bringing together said previously formed cover unit and said previously formed backsheet unit and then adhesively bonding outer portions of the bottom side of said cover unit to portions of the topside of said continuous backsheet (2), the absorbent cores (3) being interposed centrally between the bottom side of said topsheet (1) and the topside of said backsheet (2); and (f) said outer side portion of each elastic flap (5) extending laterally beyond the side edge of the topsheet (1) and terminating at least as far as the outer side edge of the backsheet (2); said laterally extending portion of the elastic flap (5) being bonded along a line (10) to the backsheet (2) and the portion of the elastic flap (5) that contains the elastic band (7) being located inwardly of said line (10).

2. The method according to claim 1 wherein bonding of the elastic flaps (5) to the topsheet (1) is achieved by at least one adhesive applied line (9, 10) and one welded line (8) extending longitudinally of these components, said welded line (8) being located inwardly relative to said at least one adhesive applied line (9).

3. The method according to claim 1 wherein the elastic flap (5) comprises a substantially non-elastic sheet that at least partially surrounds a stretched elastic band (7).

4. The method according to claim 1 wherein bonding of the elastic flap (5) to the topsheet (1) is performed so that the elastic flap (5) has an outer side portion which extends outwardly as far as the outer side edge of the backsheet (2).

* * * * *